(12) United States Patent
Damha et al.

(10) Patent No.: US 8,178,348 B2
(45) Date of Patent: *May 15, 2012

(54) CHIMERIC ANTISENSE OLIGONUCLEOTIDES OF ARABINOFURANOSE ANALOGUE AND DEOXYRIBOSE NUCLEOTIDES

(75) Inventors: Masad Jose Damha, St. Hubert (CA); Michael A. Parniak, Pittsburgh, PA (US); Chun-Nam Lok, Shek Tong Shui (HK); Ekaterina Vlazovkina, Montreal (CA)

(73) Assignee: McGill University, Montreal, Quebec (CA)

(*) Notice: Subject to any disclaimer, the term of this patent is extended or adjusted under 35 U.S.C. 154(b) by 905 days.

This patent is subject to a terminal disclaimer.

(21) Appl. No.: 10/363,768

(22) PCT Filed: Sep. 4, 2001

(86) PCT No.: PCT/CA01/01252
§ 371 (c)(1),
(2), (4) Date: Jun. 13, 2003

(87) PCT Pub. No.: WO02/20773
PCT Pub. Date: Mar. 14, 2002

(65) Prior Publication Data
US 2004/0038399 A1  Feb. 26, 2004

Related U.S. Application Data

(60) Provisional application No. 60/230,414, filed on Sep. 6, 2000.

(51) Int. Cl.
*C12N 5/00* (2006.01)
*C12N 5/02* (2006.01)
*C12N 15/11* (2006.01)
*C07H 21/04* (2006.01)

(52) U.S. Cl. .................. 435/375; 514/44 A; 536/23.2; 536/24.5

(58) Field of Classification Search .................. None
See application file for complete search history.

(56) References Cited

U.S. PATENT DOCUMENTS 5,808,040 A * 9/1998 Chu et al. ............... 536/25.3
5,955,589 A * 9/1999 Cook et al. .............. 536/23.1
5,968,748 A * 10/1999 Bennett et al. .............. 435/6

FOREIGN PATENT DOCUMENTS

WO    WO 9950409 A1 * 10/1999
WO    WO 99/67378     12/1999
WO    WO 9967378 A1 * 12/1999

OTHER PUBLICATIONS

Agrawal et al. Molecular Medicine Today. 2000, vol. 6, pp. 72-81.*
Jen et al. Stem Cells. 2000, vol. 18, pp. 307-319.*
Damha, etal. (1998) J. Am. Chem. Soc., vol. 120, 12976-12977.*
Manoharan (1999) Biochimica et Biophysica Acta, vol. 1489, pp. 117-130.*
Gotfredsen et al. (Bioorganic & Medicinal Chemistry, vol. 4, No. 8, pp. 1217-1225, 1996).*
Kois et al. (1993, Nucleic Acids Symposium Series No. 29:214-6).*
Wilds, et al. (2000, Nucleic Acids Res., v.28:3625-35).*
Zhao, G. et al., "Effect of Different Chemically Modified Oligodeoxynuclotides on Immune Stimulation." Biochem. Pharmacol. 51:173-182, 1996.
Crooke, S.T. et al., "Pharmacokinetic Properties of Several Novel Oligonucleotide Analogs in mice." J. Pharmcol. Exp. Ther 277(2):923-937, 1996.
Monia, P.B. et al., "Antitumor activity of a phosphorothioate antisense oligodeoxynucleotide targeted against C-raf kinase." Nature Medicine 2(6):668-675, 1996.
Damha, M.J. et al., "Hybrids of RNA and Arabinonucleic Acids (ANA and 2'F-ANA) Are Substrates of Ribonuclease H." J. Am. Chem. Soc. 120:12976-12977, 1998.
Noronha, A.M. et al., "Synthesis and Biophysical Properties of Arabinonucleic Acids (ANA): Circular Dichroic Spectra, Melting Temperatures, and Ribonuclease H Susceptibility of ANA-RNA Hybrid Duplexes." Biochemistry 39:7050-7062, 2000.
Giannaris, P.A. and Damha, M.J., "Hybridization properties of oligoarabinonucleotides." Can. J. Chem. 72:909-918, 1994.
Kois, P. et al., "Synthesis and Some Properties of Modified Oligonucleotides. 2. Oligonucleotides Containing 2'-Deoxy-2'Fluoro-beta-D-Arabinofuranosyl Pyrimidine Nucleosides." Nucleosides and Nucleotides 12(10):1093-1109, 1993.
Ikeda, H et al., "The effect of two antipodal fluorine-induced sugar puckers on the conformation and stability of the Dickerson-Drew dodecamer duplex [d(CGCGAATTCGCTG)]2" Nucleic Acids Res. 26(9):2237-2244, 1998.

(Continued)

*Primary Examiner* — Janet Epps-Smith
(74) *Attorney, Agent, or Firm* — Nixon Peabody LLP; David S. Resnick; Leena H. Karttunen Contarino

(57) ABSTRACT

The present invention relates to novel oligonucleotide chimera used as therapeutic agents to selectively prevent gene transcription and expression in a sequence-specific manner. In particular, this invention is directed to the selective inhibition of protein biosynthesis via antisense strategy using oligonucleotides constructed from arabinonucleotide or modified arabinonucleotide residues, flanking a series of deoxyribose nucleotide residues of variable length. Particularly this invention relates to the use of antisense oligonucleotides constructed from arabinonucleotide or modified arabinonucleotide residues, flanking a series of deoxyribose nucleotide residues of variable length, to hybridize to complementary RNA such as cellular messenger RNA, viral RNA, etc. More particularly this invention relates to the use of antisense oligonucleotides constructed from arabinonucleotide or modified arabinonucleotide residues, flanking a series of deoxyribose nucleotide residues of variable length, to hybridize to and induce cleavage of (via RNaseH activation) the complementary RNA.

21 Claims, 5 Drawing Sheets

OTHER PUBLICATIONS

Monia, BP et al., "Evaluation of 2'-Modified Oligonucleotides Containing 2'-Deoxy Gaps as Antisense Inhibitors of Gene Expression." J. Biol. Chem. 268(19):14514-14522, 1993.

Shen, L.X. et al., "Impact of Mixed-backbone Oligonucleotides on Target Binding Affinity and Target Cleaving Specificity and Selectivity by *Escherichia coli* RNase H." Bioorganic & Medical Chemistry 6:1695-1705, 1998.

Agrawal, S. and Kandimalla, E.R., "Antisense therapeutics: is it as simple as complementary base recognition?" Mol. Med. Today 6:72-81, 2000.

MacKellar, C et al., "Synthesis and physical properties of anti-HIV antisense oligonucleotides bearing terminal lipophilic groups." Nuc. Acids Res. 20(13):3411-3417, 1992.

Manoharan, M et al., "Lipidic Nucleic Acids." Tet. Lett 36(21):3651-3654, 1995.

Boffa, LC et al., "Dihydrotestosterone as a Selective Cellular/Nuclear Localization Vector for Anti-Gene Peptide Nucleic Acid in Prostatic Carcinoma Cells." Cancer Res 60:2258-2262, 2000.

Damha, Masad, et al., "Antisense L/D-Oligonucleotide Chimeras: Nuclease Stability, Base-Pairing Properties, and Activity at Directing Ribonuclease H," Biochemistry, 33:7877-7885 (33), (1994).

Tazawa, Ichiro, et al., "L-Adenylyl-(3'-5')-L-adenosine and L-Adenylyl-(2'-5')-L-adenosine," Biochemistry, 9(18):3499-3514 (1970).

Wu, Anna Fang, et al., "L-Uridine: Synthesis and Behavior as Enzyme Substrate," Biochemistry, 63:1222-1226 (1969).

Wilds, et al. (1999) Bioconjugate Chem. vol. 10, pp. 299-305.

Damha et al. (1998) J. Am. Chem. Soc. vol. 120, pp. 12976-12977.

Giannaris, et al. (1994) Can. J. Chem. vol. 72, pp. 909-917.

Manoharan, M. (1999) Biochimica et Biophsica Acta vol. 1489, pp. 117-130.

Wilds et al. (2000) Nucleic Acids Research vol. 28, No. 18, pp. 3625-3635.

\* cited by examiner

PS-DNA

PS-FANA gapmer (10 DNA)

0   15   30   60   125   250 antisense concentration (nM)

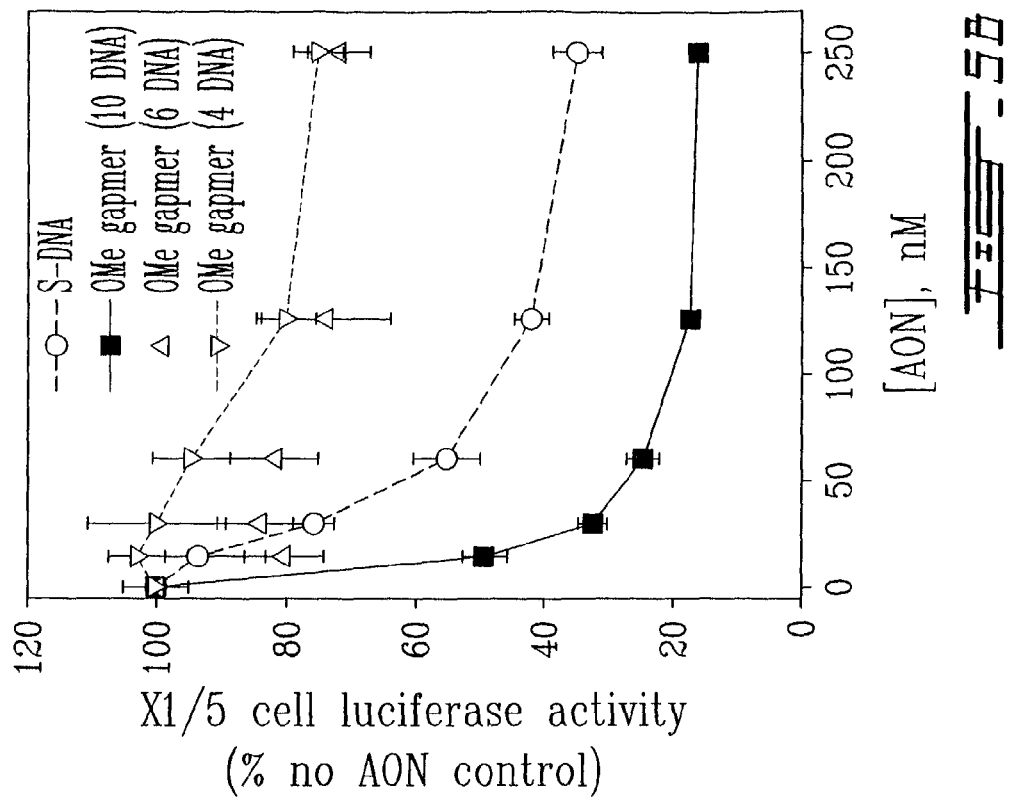
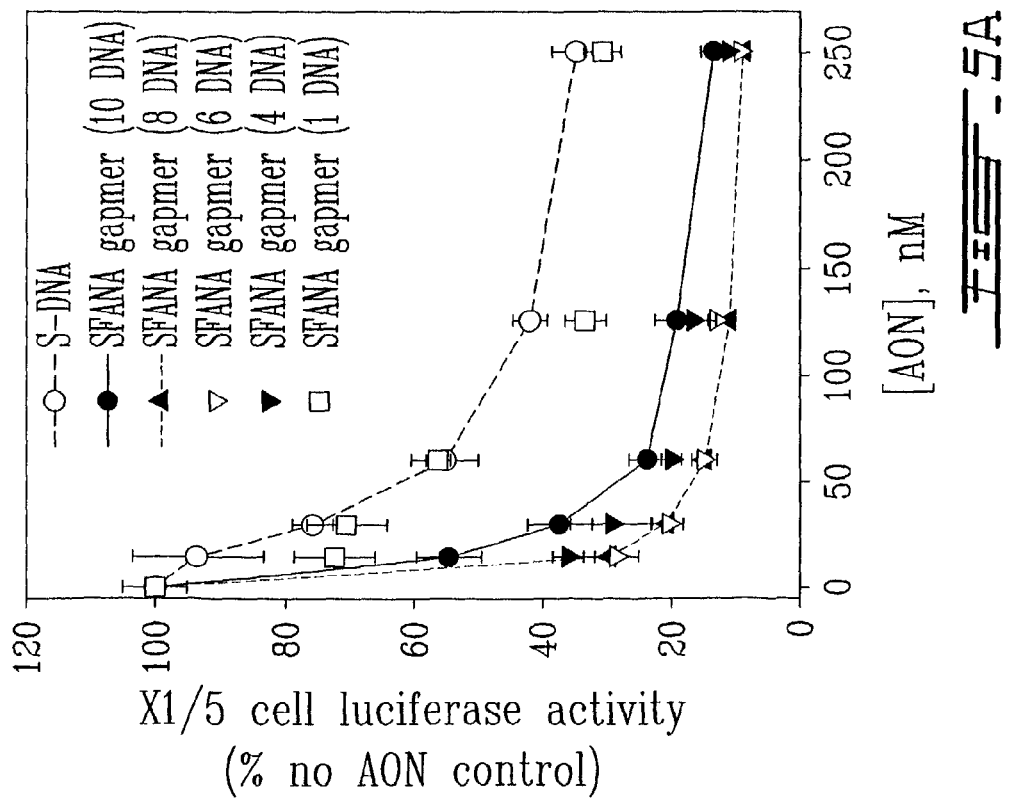

SEQUENCE LISTING

```
<160> NUMBER OF SEQ ID NOS: 13

<210> SEQ ID NO 1
<211> LENGTH: 18
<212> TYPE: DNA
<213> ORGANISM: Artificial Sequence
<220> FEATURE:
<223> OTHER INFORMATION: antisense oligonucleotide
<220> FEATURE:
<221> NAME/KEY: misc_feature
<222> LOCATION: (1)...(18)
<223> OTHER INFORMATION: containing phosphothiate bonds
<220> FEATURE:
<221> NAME/KEY: misc_feature
<222> LOCATION: (1)...(4)
<223> OTHER INFORMATION: antisense sequence
<220> FEATURE:
<221> NAME/KEY: misc_feature
<222> LOCATION: (15)...(18)
<223> OTHER INFORMATION: antisense sequence

<400> SEQUENCE: 1
atatccttgt cgtatccc                                                 18

<210> SEQ ID NO 2
```

<400> SEQUENCE: 2

000

<210> SEQ ID NO 3
<400> SEQUENCE: 3

000

<210> SEQ ID NO 4
<400> SEQUENCE: 4

000

<210> SEQ ID NO 5
<400> SEQUENCE: 5

000

<210> SEQ ID NO 6
<400> SEQUENCE: 6

000

<210> SEQ ID NO 7
<400> SEQUENCE: 7

000

<210> SEQ ID NO 8
<400> SEQUENCE: 8

000

<210> SEQ ID NO 9
<400> SEQUENCE: 9

000

<210> SEQ ID NO 10
<400> SEQUENCE: 10

000

<210> SEQ ID NO 11
<400> SEQUENCE: 11

000

<210> SEQ ID NO 12
<400> SEQUENCE: 12

000

<210> SEQ ID NO 13
<211> LENGTH: 18
<212> TYPE: DNA
<213> ORGANISM: Artificial Sequence

```
<220> FEATURE:
<223> OTHER INFORMATION: randomized oligonucleotide

<400> SEQUENCE: 13
taatccctat cgtcgctt                                                18
```

CHIMERIC ANTISENSE OLIGONUCLEOTIDES OF ARABINOFURANOSE ANALOGUE AND DEOXYRIBOSE NUCLEOTIDES

CROSS REFERENCE TO RELATED APPLICATIONS

This application is a National Phase Entry Application under 35 U.S.C. §371 of International Application No. PCT/CA01/01252, filed Sep. 4, 2001, which designated the United States, and which claims benefit under 35 U.S.C. §119(e) of a U.S. provisional application Ser. No. 61/230,414.

BACKGROUND OF THE INVENTION (a) Field of the Invention

The invention relates to novel oligonucleotide chimera used as therapeutic agents to selectively prevent gene transcription and expression in a sequence-specific manner. In particular, this invention is directed to the selective inhibition of protein biosynthesis via antisense strategy using oligonucleotides constructed from arabinonucleotide or modified arabinonucleotide residues, flanking a series of deoxyribose nucleotide residues of variable length. Particularly this invention relates to the use of antisense oligonucleotides constructed from arabinonucleotide or modified arabinonucleotide residues, flanking a series of deoxyribose nucleotide residues of variable length, to hybridize to complementary RNA such as cellular messenger RNA, viral RNA, etc. More particularly this invention relates to the use of antisense oligonucleotides constructed from arabinonucleotide or modified arabinonucleotide residues, flanking a series of deoxyribose nucleotide residues of variable length, to hybridize to and induce cleavage of (via RNaseH activation) the complementary RNA.

(b) Description of Prior Art

The Antisense Strategy

Antisense oligonucleotides (AON) are therapeutic agents that can inhibit specific gene expression in a sequence-specific manner. Many AON are currently in clinical trials for the treatment of cancer and viral diseases. For clinical utility, AON should exhibit stability against degradation by serum and cellular nucleases, show low non-specific binding to serum and cell proteins (since this binding would diminish the amount of antisense oligonucleotide available to base-pair with the target RNA), exhibit enhanced recognition of the target RNA sequence (in other words, provide increased stability of the antisense-target RNA duplex at physiological temperature), and to some extent, demonstrate cell-membrane permeability. Antisense inhibition of target gene expression is believed to occur by at least two main mechanisms. The first is "translation arrest", in which the formation of a duplex between the antisense oligomer and its target RNA prevents the complete translation of that RNA into protein, by blocking the ability of the ribosome to recognize the complete mRNA sequence. The second, and probably more important, mechanism concerns the ability of the antisense oligonucleotide to direct the ribonuclease H (RNaseH) catalyzed degradation of the target mRNA. RNaseH is an endogenous cellular enzyme that specifically degrades RNA when it is duplexed with a complementary DNA oligonucleotide (or antisense oligonucleotide) component. For example, when an antisense DNA oligonucleotide hybridizes to a cellular mRNA via complementary base pairing, cellular RNaseH recognizes the resulting DNA/RNA hybrid duplex and then degrades the mRNA at that site. Antisense oligonucleotides that can modulate gene expression by both mechanisms are highly desirable as this increases the potential efficacy of the antisense compound in vivo.

Oligonucleotide Analogs

Oligonucleotides containing natural (ribose or deoxyribose) sugars and phosphodiester (PO) linkages are rapidly degraded by serum and intracellular nucleases, which limits their utility as effective therapeutic agents. Chemical strategies to improve nuclease stability include modification of the sugar moiety, the base moiety, and/or modification or replacement of the internucleotide phosphodiester linkage. To date, the most widely studied analogues are the phosphorothioate (PS) oligodeoxynucleotides, in which one of the non-bridging oxygen atoms in the phosphodiester backbone is replaced with a sulfur. Numerous S-DNA oligonucleotide analogues are undergoing clinical trial evaluation for the treatment of cancer, infectious diseases and other human pathologies, and some are already subjects of New Drug Application (NDA) filings. S-DNA antisense are able to elicit RNaseH degradation of the target mRNA and they are reasonably refractory to degradation by serum and cellular nucleases. However, PS-DNA antisense tend to form less thermodynamically-stable duplexes with the target RNA nucleic acid than oligodeoxynucleotides with phosphodiester (PO) linkages. Furthermore, S-DNA antisense can be less efficient at eliciting RNaseH degradation of the target RNA than the corresponding PO-DNA.

Specificity of action may be improved by developing novel oligonucleotide analogues. Current strategies to generate novel oligonucleotides are to alter the internucleotide phosphate backbone, the heterocyclic base, and the sugar ring, or a combination of these. Alteration or complete replacement of the internucleotide linkage has been the most popular approach, with over 60 types of modified phosphate backbones studied since 1994. Apart from the phosphorothioate backbone, only two others have been reported to activate RNaseH activity, i.e., the phosphorodithioate ($PS_2$) and the boranophosphonate backbones. Because of the higher sulfur content of phosphorodithioate-linked ($PS_2$) oligodeoxynucleotides, they appear to bind proteins tighter than the phosphorothioate (PS) oligomers, and to activate RNaseH mediated cleavage with reduced efficiency compared to the PS analogue. Boranophosphonate-linked oligodeoxynucleotides activate RNaseH mediated cleavage of RNA targets, but less well than PO- or PS-linked oligodeoxynucleotides.

Among the reported sugar-modified oligonucleotides most of them contain a five-membered ring, closely resembling the sugar of DNA (D-2-deoxyribose) and RNA (D-ribose). Example of these are α-oligodeoxynucleotide analogs, wherein the configuration of the 1' (or anomeric) carbon has been inverted. These analogues are nuclease resistant, form stable duplexes with DNA and RNA sequences, and are capable of inhibiting β-globin mRNA translation via an RNaseH-independent antisense mechanism. Other examples are xylo-DNA, 2'-O-Me RNA and 2'-F RNA. These analogues form stable duplexes with RNA targets, however, these duplexes are not substrates for RNaseH. To overcome this limitation, mixed-backbone oligonucleotides ("MBO") composed of either phosphodiester (PO) and phosphorothioate (PS) oligodeoxynucleotide segments flanked on both sides by sugar-modified oligonucleotide segments have been synthesized (Zhao, G. et al., *Biochem. Pharmacol.* 1996, 51, 173; Crooke, S. T. et al. *J. Pharmacol. Exp. Ther.* 1996, 277, 923). Among the MBOs most studied to date is the [2'-OMe RNA]-[PS DNA]-[2'OMe RNA] chimera The PS segment in the middle of the chain serves as the RNaseH activation domain, whereas the flanking 2'-OMe RNA regions increases affinity of the MBO strand for the target RNA. MBOs have increased stability in vivo, and appear to be more effective than phosphorothioate analogues in their biological activity both in vitro and in vivo. Examples of this approach incorporating 2'-OMe and other alkoxy substituents in the flanking regions of an oligonucleotide have been demonstrated by Monia et al. by enhanced antitumor activity in vivo (Monia, P. B. et al. *Nature Med.* 1996, 2, 668). Several pre-clinical trials with these analogues are ongoing.

The synthesis of oligonucleotides containing hexopyranoses instead of pentofuranose sugars has also been reported. A few of these analogues have increased enzymatic stability but generally suffer from a reduced duplex forming capability with the target sequence. A notable exception is 6'→4' linked oligomers constructed from 1,5-anhydrohexitol units which, due to their highly pre-organized sugar structure, form very stable complexes with RNA. However, none of these hexopyranose oligonucleotide analogues have been shown to elicit RNaseH activity. Recently, oligonucleotides containing completely altered backbones have been synthesized. Notable examples are the peptide nucleic acids ("PNA") with an acyclic backbone. These compounds have exceptional hybridization properties, and stability towards nucleases and proteases. However, efforts to use PNA oligomers as antisense constructs have been hampered by poor water solubility, self-aggregation properties, poor cellular uptake, and inability to activate RNaseH. Very recently, PNA-[PS-DNA]-PNA chimeras have been designed to maintain RNaseH mediated cleavage via the PS-DNA portion of the chimera.

Arabinonucleosides and Arabinonucleic Acids (ANA)

Arabinonucleosides are isomers of ribonucleosides, differing only in the stereochemistry at the 2'-position of the sugar ring. We have previously shown that antisense oligonucleotides constructed entirely from nucleotides comprising arabinose or modified arabinose (especially 2'-F arabinose) sugars are able to elicit RNaseH degradation of the complementary target RNA (Damha, M. J. et al. *JACS* 1998, 120, 12976; Noronha, A. M. et al. *Biochemistry* 2000, 39, 7050). We also noted that the thermal stability of duplexes consisting of an arabinose oligonucleotide with RNA was less than that of the analogous DNA/RNA duplex (Noronha, A. M. et al. *Biochemistry* 2000, 39, 7050). In contrast however, the thermal stability of duplexes consisting of an oligonucleotide synthesized with 2'-F arabinose nucleotides hybridized with RNA is generally greater than that of the analogous DNA/RNA duplex (Damha, M. J. et al. *JACS* 1998, 120, 12976). Giannaris and Damha found that replacement of the phosphodiester (PO) linkage in ANA oligonucleotides with phosphorothioate (PS) linkages significantly decreased the stability of the PS-ANA/PO-RNA duplex (Giannaris, P. A.; Damha, M. J. *Can. J. Chem.* 1994, 72, 909). This destabilization was greater than that observed when the PO linkages of an analogous DNA oligonucleotide were replaced with S internucleotide linkages (Giannaris, P. A.; Damha, M. J. *Can. J. Chem.* 1994, 72, 909).

Watanabe and co-workers incorporated 2'-deoxy-2'-fluoro-□-D-arabinofuranosylpyrimidine nucleosides (2'-F-ara-N, where N=C, U and T) at several positions within an oligonucleotide primarily comprised of a PO-DNA chain and evaluated the hybridization properties of such (2'-F)ANA-DNA "chimeras" towards complementary DNA (Kois, P. et al. *Nucleosides & Nucleotides* 1993, 12, 1093). Substitutions with 2'-F-araU and 2'-F-araC destabilized duplex stability compared to the all-DNA/RNA duplex, whereas substitutions with 2'-F-araT stabilized the duplex. Marquez and co-workers recently evaluated the self-association of a DNA strand in which two internal thymidines were replaced by 2'-F-araT's (Ikeda et al. *Nucleic Acids Res.* 1998, 26, 2237). They confirmed the findings of Watanabe and co-workers that internal 2'-F-araT residues stabilize significantly the DNA double helix. The association of these (2'-F)ANA-DNA "chimeras" with complementary RNA (the typical antisense target) was not reported.

Elicitation of Cellular RNaseH Degradation of Target RNA by Antisense Oligonucleotides One of the most important mechanisms for antisense oligonucleotide directed inhibition of gene expression is the ability of these antisense oligonucleotides to form a structure, when duplexed with the target RNA, that can be recognized by cellular RNaseH. This enables the RNaseH-mediated degradation of the RNA target, within the region of the antisense oligonucleotide-RNA base-paired duplex (Monia et al. *J. Biol. Chem.* 1993, 268, 14514).

RNase H selectively degrades the RNA strand of a DNA/RNA heteroduplex. RNaseH1 from the bacterium *Escherichia coli* is the most readily available and the best characterized enzyme. Studies with eukaryotic cell extracts containing RNase H suggest that both prokaryotic and eukaryotic enzymes exhibit similar RNA-cleavage properties, although the bacterial enzyme is better able to cleave duplexes of small length (Monia et al. *J. Biol. Chem.* 1993, 268, 14514). *E. coli* RNaseH1 is thought to bind in the minor groove of the DNA/RNA double helix and to cleave the RNA by both endonuclease and processive 3'-to-5' exonuclease activities. The efficiency of RNase H degradation displays minimal sequence dependence and is quite sensitive to chemical changes in the antisense oligonucleotide. For example, while RNaseH readily degrades RNA in S-DNA/RNA duplexes, it cannot do so in duplexes comprising methylphosphonate-DNA, α-DNA, or 2'-OMe RNA antisense oligonucleotides with RNA. Furthermore, while *E. coli* RNaseH binds to RNA/RNA duplexes, it cannot cleave either RNA strand, despite the fact that the global helical conformation of RNA/RNA duplexes is similar to that of DNA/RNA substrate duplexes ("A"-form helices). These results suggest that local structural differences between DNA/RNA (substrate) and RNA/RNA (substrate) duplexes contribute to substrate discrimination.

Arabinonucleic Acids as Activators of RNaseH Activity

An essential requirement in the antisense approach is that an oligonucleotide or its analogue recognize and bind tightly to its complementary target RNA. The ability of the resulting antisense oligonucleotide/RNA duplex to serve as a substrate of RNaseH is likely to have therapeutic value by enhancing the antisense effect relative to antisense oligonucleotides that are unable to activate this enzyme. Apart from PS-DNA (phosphorothioates), $PS_2$-DNA (phosphorodithioates), boranophosphonate-linked DNA, and MBO oligos containing an internal PS-DNA segment, the only examples of fully modified oligonucleotides that elicit RNaseH activity are those constructed from arabinonucleotide (ANA) or modified arabinonucleotide residues (International Application published under No. WO 99/67378; Damha, M. J. et al. *JACS* 1998, 120, 12976; Noronha, A. M. et al. *Biochemistry* 2000, 39, 7050). These ANA oligonucleotides retain the natural β-D-furanose configuration and mimic the conformation of DNA strands (e.g., with sugars puckered in the C2'-endo conformation). The latter requirement stems from the fact that the antisense strand of natural substrates is DNA, and as indicated above, its primary structure (and/or conformation) appears to be essential for RNaseH/substrate cleavage; the DNA sugars of DNA/RNA hybrids adopt primarily the C2'-endo conformation. ANA is a stereoisomer of RNA differing only in the stereochemistry at the 2'-position of the sugar ring. ANA/RNA duplexes adopt a helical structure that is very similar to that of DNA/RNA substrates ("A"-form), as shown by similar circular dichroism spectra of these complexes (Damha, M. J. et al. *JACS* 1998, 120, 12976; Noronha, A. M. et al. *Biochemistry* 2000, 39, 7050).

Mixed-backbone or "Gapmer" Oligonucleotide Constructs as Antisense Oligonucleotides Mixed-backbone oligonucleotides (MBO) composed of a phosphodiester or phosphorothioate oligodeoxynucleotide "gap" segment flanked at both the 5'- and 3'-ends by sugar-modified oligonucleotide "wing" segments have been synthesized (Zhao, G. et al., *Biochem. Pharmacol.* 1996, 51, 173; Crooke, S. T. et al. *J. Pharmcol. Exp. Ther.* 1996, 277, 923). Probably the most studied MBO to date is the [2'-OMe RNA]-[PS DNA]-[2'OMe RNA] chimera. Oligonucleotides comprised of 2'-OMe RNA alone bind with very high affinity to target RNA, but are unable to elicit RNaseH degradation of that target RNA. In [2'-OMe RNA]-[PS DNA]-[2'OMe RNA] chimera oligonucleotides, the PS-DNA segment in the middle of the chain serves to elicit RNaseH degradation of the target, whereas the flanking 2'-OMe RNA "wing" regions increase the affinity of the MBO strand for the target RNA. MBOs have increased stability in vivo, and appear to be more effective than same-sequence PS-DNA analogues in their biological activity both in vitro and in vivo. Examples of this approach incorporating 2'-OMe and other alkoxy substituents in the flanking regions of an oligonucleotide have been demonstrated by Monia et al. by enhanced antitumor activity in vivo (Monia, P. B. et al. *Nature Med.* 1996, 2, 668). Several pre-clinical trials with these analogues are ongoing.

Nonetheless, because 2'-OMe RNA cannot elicit RNaseH activity, the DNA gap size of the [2'-OMe RNA]-[PS DNA]-[2'OMe RNA] chimera oligonucleotides must be carefully defined While *E. coli* RNaseH can recognize and use 2'-OMe RNA MBO with DNA gaps as small as 4 DNA nucleotides (Shen, L. X. et al 1998 *Biorg. Med. Chem.* 6, 1695), the eukaryotic RNaseH (such as human RNaseH) requires substantially larger DNA gaps (7 DNA nucleotides or more) for optimal degradation activity (Monia, B. P. et al 1993 *J. Biol. Chem.* 268, 14514). In general, with [2'-OMe RNA]-[PS DNA]-[2'OMe RNA] chimera oligonucleotides, eukaryotic RNaseH-mediated target RNA cleavage efficiency decreases with decreasing DNA gap length, and becomes increasingly negligible with DNA gap sizes of less than 6 DNA nucleotides. Thus, antisense activity of [2'-OMe RNA]-[PS DNA]-[2'OMe RNA] chimera oligonucleotides is highly dependent on DNA gap size (Monia, B. P. et al 1993 *J. Biol. Chem.* 268, 14514; Agrawal, S. and Kandimalia, E. R 2000 *Mol. Med. Today*, 6, 72).

Recently, oligonucleotides containing completely altered backbones have been synthesized. Notable examples are the peptide nucleic acids ("PNA") with an acyclic backbone. These compounds have exceptional hybridization properties, and stability towards nucleases and proteases. However, efforts to use PNA oligomers as antisense constructs have been hampered by poor water solubility, self-aggregation properties, poor cellular uptake, and inability to activate RNaseH. Very recently, PNA-[PS-DNA]-PNA chimeras have been designed to maintain RNaseH mediated cleavage via the PS-DNA portion of the chimera It would be highly desirable to be provided with oligonucleotides constructed from arabinonucleotide or modified arabinonucleotide residues, flanking a series of deoxyribose nucleotide residues of variable length, for the sequence specific inhibition of gene expression via association to (and RNaseH mediated cleavage of) complementary messenger RNA.

SUMMARY OF THE INVENTION

One aim of the present invention is to provide antisense oligonucleotides chimera constructed from arabinonucleotide or modified arabinonucleotide residues, flanking a series of deoxyribose nucleotide residues of variable length, that form a duplex with its target RNA sequence. Such resulting antisense oligonucleotide/RNA duplex is a substrate for RNaseH, an enzyme that recognizes this duplex and degrades the RNA target portion. RNaseH mediated cleavage of RNA targets is considered to be a major mechanism of action of antisense oligonucleotides.

The present invention relates to the discovery that certain antisense hybrid chimeras, specifically those constructed from 2'-deoxy-2'-fluoro-β-D-arabinonucleotides (FANA) flanking a defined sequence constructed from β-D-2'-deoxyribonucleotides (DNA), are superior to antisense hybrid chimeras constructed from 2'-O-methyl-β-D-ribonucleotides (OMeNA) flanking a defined sequence constructed from β-D-2'-deoxyribonucleotides (DNA).

Accordingly, antisense hybrid chimeras constructed from 2'-deoxy-2'-fluoro-β-D-arabinonucleotides (FANA) flanking a defined sequence constructed from β-D-2'-deoxyribonucleotides (DNA), have potential utility as therapeutic agents and/or tools for the study and control of specific gene expression in cells and organisms.

In accordance with the present invention there is provided an oligonucleotide 'chimera' to selectively prevent gene expression in a sequence-specific manner, which comprises a chimera of modified arabinose and 2'-deoxy sugars hybridizing to a single stranded RNA to induce at least one of the following: (a) nuclease stability, (b) binding strength of hybridization to complementary RNA sequences, (c) permeability of said oligonucleotide into cells; (d) cleavage of target RNA by RNaseH; or (e) physical blockage of ribose translocation ("translation arrest").

Such an oligonucleotide has a general backbone composition of "[FANA WING]-[DNA GAP]-[FANA WING]", or 5'RO(FANA-p)x-(DNA-p)y-(FANA-p)z-(FANA)3'OH, and more precisely has the general structure:

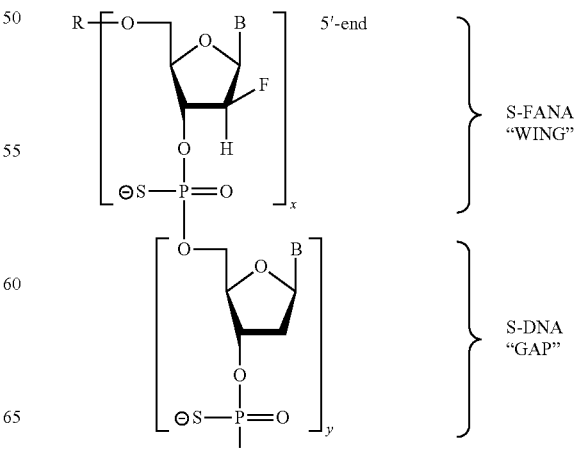

-continued

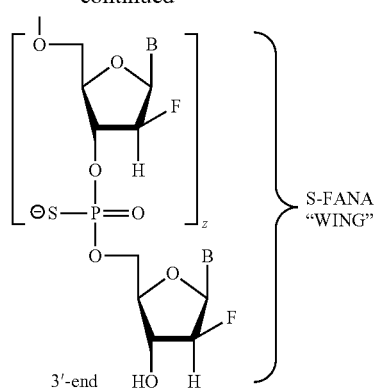

wherein, x≧1, y≧1, and z≧0, and

R is selected from a group consisting of hydrogen, thiophosphate, and a linker moiety that enhances cellular uptake of such oligonucleotide.

In accordance with the present invention there is provided an oligonucleotide which has the formula:

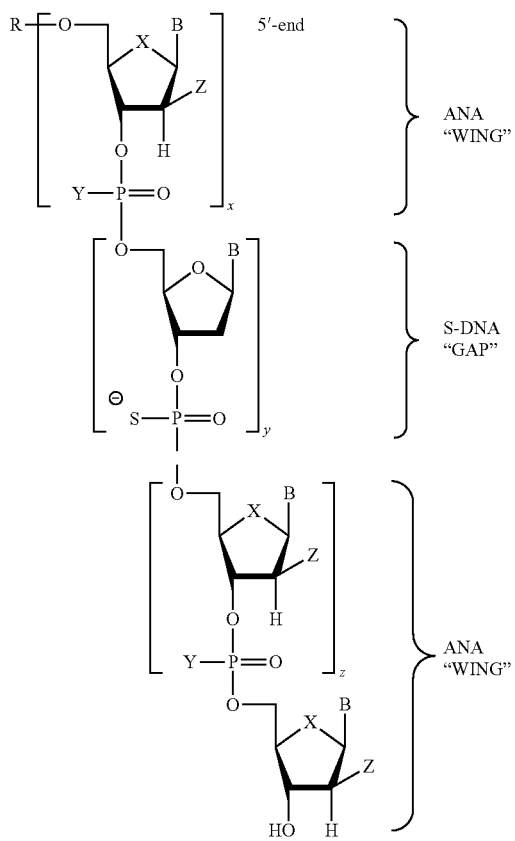

wherein, x≧1, y≧1, and z≧0;

R is selected from a group consisting of hydrogen, thiophosphate, and a linker moiety that enhances cellular uptake of such oligonucleotide;

B is selected from the group consisting of adenine, guanine, uracil, thymine, cytosine, inosine, and 5-methylcytosine;

Y at the internucleotide phosphate linkage is selected from the group consisting of sulfur, oxygen, methyl, amino, alkylamino, dialkylamino (the alkyl group having one to about 20 carbon atoms), methoxy, and ethoxy;

X at the furanose ring (position 4') is selected from the groups oxygen, sulfur, and methylene (CH$_2$); and Z at the 2' position of the sugar ring is selected from the group consisting of a halogen (fluorine, chlorine, bromine, iodine), alkyl, alkylhalide (e.g., —CH$_2$F), allyl, amino, aryl, alkoxy, and azido.

In accordance with the present invention there is provided an oligonucleotide which has the formula:

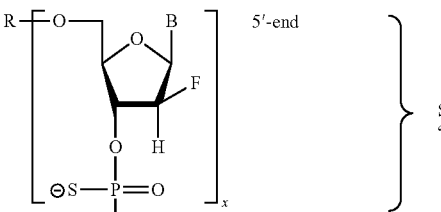

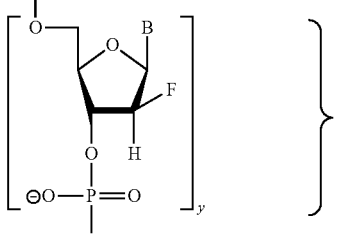

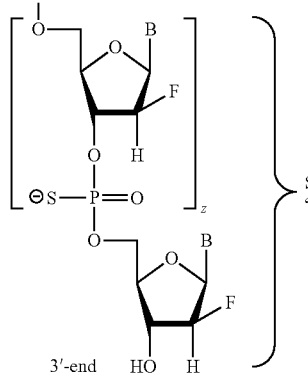

wherein, x≧1, y≧1, and z≧0;

R is selected from a group consisting of hydrogen, thiophosphate, and a linker moiety that enhances cellular uptake of such oligonucleotide;

B is selected from the group consisting of adenine, guanine, uracil, thymine, cytosine, inosine, and 5-methylcytosine.

In accordance with the present invention there is provided an oligonucleotide which has the formula:

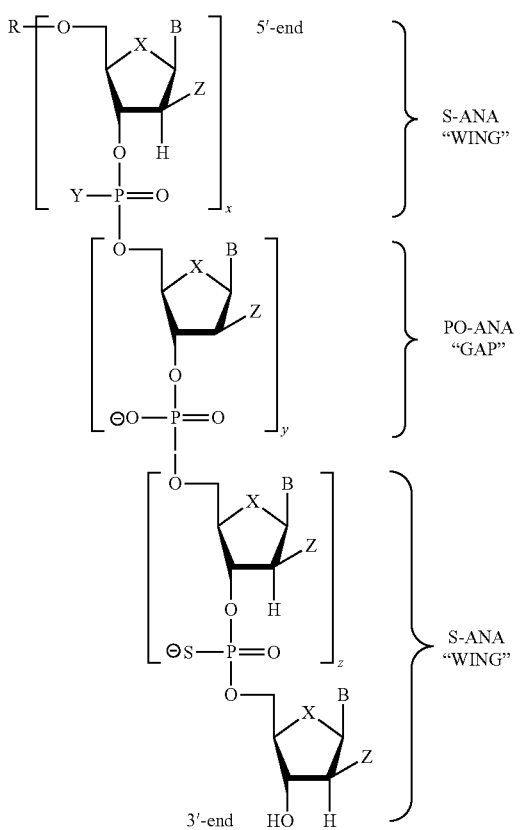

wherein, x≧1, y≧1, and z≧0;

R is selected from a group consisting of hydrogen, thiophosphate, and a linker moiety that enhances cellular uptake of such oligonucleotide;

B is selected from the group consisting of adenine, guanine, uracil, thymine, cytosine, inosine, and 5-methylcytosine;

Y at the internucleotide phosphate linkage is selected from the group consisting of sulfur, oxygen, methyl, amino, alkylamino, dialkylamino (the alkyl group having one to about 20 carbon atoms), methoxy, and ethoxy;

X at the furanose ring (position 4') is selected from the groups oxygen, sulfur, and methylene ($CH_2$); and Z at the 2' position of the sugar ring is selected from the group consisting of a halogen (fluorine, chlorine, bromine, iodine), hydroxyl, alkyl, alkyihalide (e.g., —$CH_2F$), allyl, amino, aryl, alkoxy, and azido.

In accordance with the present invention there is provided a method for cleaving single stranded RNA, which comprises the steps of:

(a) hybridizing in a sequence specific manner an oligonucleotide of the present invention to a single stranded RNA to induce RNase H activity, and (b) allowing said induced RNase H to cleave said hybridized single stranded RNA.

In accordance with the present invention there is provided a method to prevent translation of said single stranded RNA, which comprises hybridizing in a sequence specific manner chimeric oligonucleotides of claims 2 to 5 to single stranded RNA, and thereby prevent production of specific protein encoded by said single stranded RNA.

The RNA may be complementary RNA, such as cellular mRNA or viral RNA.

In accordance with the present invention there is provided the use of an oligonucleotide of the present invention for the preparation of a medicament for cleaving single stranded RNA, wherein said oligonucleotide hybridizes in a sequence specific manner to a single stranded RNA to induce RNase H activity in cleaving said hybridized single stranded RNA.

In accordance with the present invention there is provided the use of an oligonucleotide of the present invention for the preparation of a probe or laboratory reagent for cleaving single stranded RNA, wherein said oligonucleotide hybridizes in a sequence specific manner to a single stranded RNA to induce RNase H activity in cleaving said hybridized single stranded RNA In accordance with the present invention there is provided a composition to selectively prevent gene expression in a sequence-specific manner; which comprises an effective amount of an oligonucleotide 'chimera' of the present invention in association with a pharmaceutically acceptable carrier.

BRIEF DESCRIPTION OF THE DRAWINGS

FIG. 5 illustrates the effect of DNA "gap" size on the ability of gapmer antisense oligonucleotides to inhibit cellular specific gene expression—effect of antisense oligonucleotide concentration

DETAILED DESCRIPTION OF THE INVENTION

Figure 1:
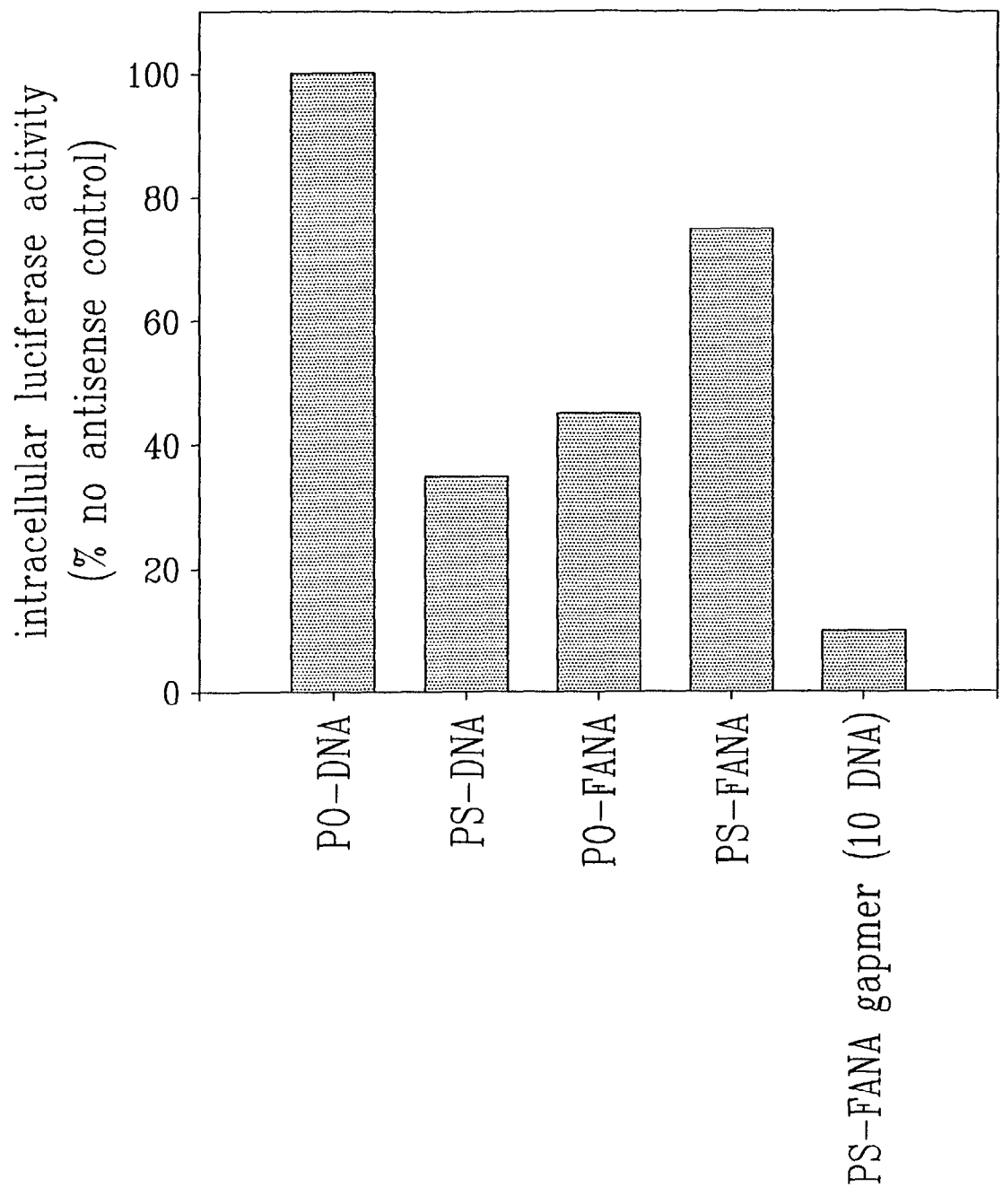
FIG. 1 illustrates the efficacy of various antisense oligonucleotides to inhibit intracellular gene expression.

In accordance with the present invention, there is provided antisense oligonucleotides constructed constructed from nucleotides possessing β-D-arabinose or modified β-D-arabinose sugar moieties, flanking a series of deoxyribose nucleotide residues of variable length, that form a duplex with its target RNA sequence. from β-D-arabinose and its derivatives and the therapeutic use of such compounds. It is the object of the present invention to provide new antisense oligonucleotide analogues that hybridize to complementary nucleic acids which may be mRNA or viral RNA (including retroviral RNA), for the purpose of inhibiting the expression of specific genes. More particularly this invention relates to the use of antisense oligonucleotides constructed constructed from nucleotides possessing β-D-arabinose or modified β-D-arabinose sugar moieties, flanking a series of deoxyribose nucleotide residues of variable length, to hybridize to specific target RNA sequences and elicit the cleavage of said target RNA through the action of cellular RNaseH.

The oligonucleotides of this invention may be represented by the following formula (I):

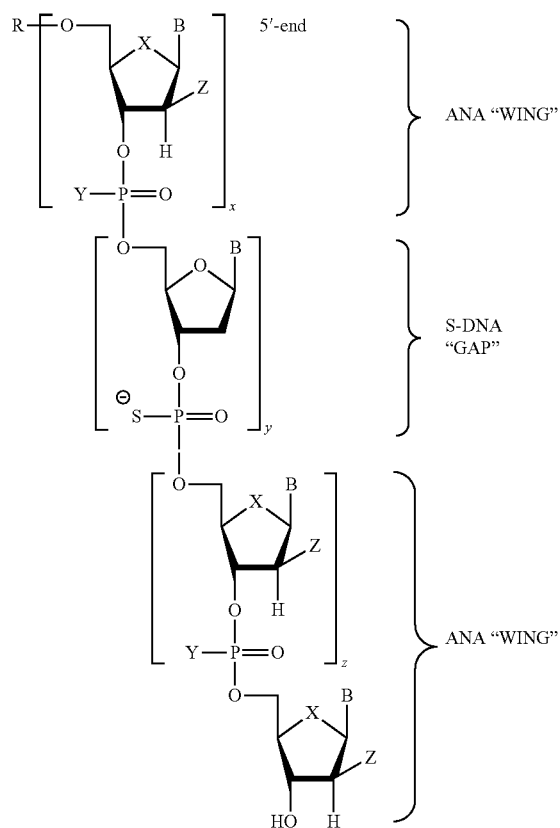

where B includes but it is not necessarily limited to a common purine or pyrimidine base such as adenine, guanine, cytosine, thymine, and uracil. The oligonucleotides include stretches of DNA (DNA "gap") flanked by a number of β-D-arabinofuranose or modified β-D-arabinofuranose nucleotides at the 5'- and 3'-ends ("wings") of the antisense oligonucleotide, thereby forming "gapmers" such as ANA-DNA-ANA, 2'F-ANA-DNA-2'F-ANA, etc. The internucleotide phosphate linkage includes but it is not necessarily limited to oxygen, sulfur, methyl, amino, alkylamino, dialkylamino, methoxy, and ethoxy. The 2'-substituent of the arabinose sugar includes but is not limited to fluorine, hydroxyl, amino, azido, methyl, methoxy and other alkoxy groups (e.g., ethoxy, proproxy, methoxyethoxy, etc.).

The gapmer antisense oligonucleotide of this invention contains a sequence that is complementary to a specific sequence of a messenger RNA, or viral genomic RNA, such that the gapmer oligonucleotide can specifically inhibit the biosynthesis of proteins encoded by the mRNA, or inhibit virus replication, respectively. Partial modifications to the oligonucleotide directed to the 5' and/or 3'-terminus, or the phosphate backbone or sugar residues to enhance their antisense properties (e.g. nuclease resistance) are within the scope of the invention.

A preferred group of oligonucleotides useful in this invention, are those wherein B is a natural base(adenine, guanine, cytosine, thymine, uracil), the sugar moiety of the "wings" is β-D-2'deoxy-2'-F-arabinofuranose, and the internucleotide phosphate linkages contain sulfur (as phosphorothioate linkages). These modifications give rise to oligonucleotides that exhibit high affinity for single stranded RNA In addition, these oligonucleotides have been shown to meet the requirements necessary for antisense therapeutics. For example, they elicit the degradation of the target RNA by cellular RNaseH, thereby decreasing the intracellular amount of and activity of the specific protein encoded by the target RNA.

The gapmer antisense oligonucleotides of this invention exhibit a number of desirable properties:
(1) They were found to bind to and cleave single stranded RNA by activating RNaseH. The gapmer oligonucleotides possessing "wings" comprised of β-D2'-deoxy-2'-F-arabinofuranose nucleotides in particular were found to have excellent affinity towards RNA targets, comparable to gapmer oligonucleotides possessing "wings" comprised of 2'-O-methylribonucleotides, and significantly better than that of identical sequence DNA.
(2) The gapmer oligonucleotides possessing "wings" comprised of β-D-2'-deoxy2'-F-arabinofuranose nucleotides were found to better effect sequence-specific inhibition of intracellular gene expression than the same-sequence DNA oligonucleotides. With large DNA gaps (10 DNA oligonucleotides), the intracellular antisense activity of gapmer oligonucleotides possessing "wings" comprised of β-D-2'deoxy-2'-F-arabinofuranose nucleotides was equivalent to that of same-sequence gapmer oligonucleotides possessing "wings" comprised of 2'-O-methylribonucleotides. With smaller DNA gaps (6 DNA or less), the intracellular antisense activity of gapmer oligonucleotides possessing "wings" comprised of β-D-2'-deoxy-2'-F-arabinofuranose nucleotides was significantly better than that of same-sequence gapmer oligonucleotides possessing "wings" comprised of 2'-O-methylribonucleotides.

These observations establish that gapmer oligonucleotides possessing "wings" comprised of β-D-2'-deoxy-2'-F-arabinofuranose nucleotides flanking an internal sequence of DNA (the "gap") are excellent models of antisense oligonucleotide agents, and should serve as therapeutics and/or valuable tools for studying and controlling gene expression in cells and organisms.

The present invention will be more readily understood by referring to the following examples which are given to illustrate the invention rather than to limit its scope.

EXAMPLE I

Preparation of Antisense Oligonucleotides Constructed from 2'-deoxy-2'-fluoro-β-D-arabinonucleotides (FANA) Flanking a Defined Sequence Constructed from β-D-2'-deoxyribonucleotides (DNA)

1. Synthesis of FANA, S-[FANA], and S-[FANA-DNA-FANA]

The synthesis of PO-FANA was conducted as previously described (Damha et al. *J. Am. Chem. Soc.* 120, 12976-12977 (1998). Synthesis of S-FANA and S-[FANA-DNA-FANA] chimeras were synthesized on a 1 micromol scale using an Expedite 8909 DNA-synthesizer. Long-chain alkylamine controlled-pore glass (LCAA-CPG) was used as the solid support. The synthesis cycle consisted of the following steps:
1) Detrylation of nucleoside/tide bound to CPG (3% trichloroacetic acid/dichloromethane): 150 sec.
2) Coupling of 2'-F-arabinonucleoside or 2'-deoxyribonucleoside 3'-phosphoramidite monomers: 15 min. Concentration of monomers used were 50 mg/mL for araF-T, araF-C and DNA monomers, and 60 mg/mL for araA and araF-G (acetonitrile as solvent).

3) Acetylation using the standard capping step: 20 sec. The capping solution consisted of 1:1 (v/v) of "capA" and "capB" reagents. CapA: acetic anhydride/collidine/THF (1:1:8 ml); cap B: N-Methylimidazole/THF (4:21 ml).
4) Extensive washing with acetonitrile (50 pulses).
5) Sulfuration with a fresh solution of 0.2M 3H-1,2-benzodithiol-3-one in acetonitrile: 10 min.
6) Washing with acetonitrile: 20 pulses.
7) Drying of the solid support by addition of the capping reagent (see step 3): 5 sec.
8) Washing with acetonitrile (20 pulses).

Following chain assembly, oligonucleotides were cleaved from the solid support and deprotected as previously described (Noronha et al. *Biochemistry* 39, 7050-7062 (2000)). The crude oligomers were purified by either (a) preparative gel electrophoresis (24% acrylamide, 7M Urea) following by desalting (Sephadex™ G-25), or (b) anion-exchange HPLC following by desalting (SepPak™ cartridges).
Yields: 5-30 $A_{260}$ units
Conditions for HPLC Purification:

| Column: | Protein Pak DEAE-5PW (7.5 mm × 7.5 cm, Waters ™), |
|---|---|
| Solvents: | Buffer A: H$_2$O; Buffer B: 1M NaClO$_4$, |
| Gradient: | 100% buffer A isocratic for 12 min, |
| | 100% A-15% B, linear (over 5 min), |
| | 15% B-55% B, linear (over 60 min). |

Loading was 1-2 $A_{260}$ units for analysis and 30-50 $A_{260}$ units for preparative separation. Flow rate was set at 1 ml/min, temperature was adjusted at 50° C. The detector was set at 260 nm for analytical and 290 nm for preparative chromatography. Under these conditions, the desired full-length oligomer eluted last 2. Synthesis of S-DNA and S-[2'OMe-RNA-DNA-2'-OMe-RNA] Chimeras Phosphorothioated DNA (S-DNA) and S-[2'OMe-RNA-DNA-2'OMe-RNA] chimeras were obtained commercially from the University of Calgary DNA Synthesis Laboratory (Calgary, ALTA). They were purified (HPLC) and desalted (SepPak™ cartridges) as described above (see part 1 above).

The base sequence and hybridization properties of the various oligonucleotides synthesized are given in Table 1.

TABLE 1

Antisense oligonucleotide (AON) sequences and melting temperatures (Tm) of duplexes of AON with complementary target RNA[a]

| ID # | AON Designation | AON Sequence[b] | Tm (° C.)[c] |
|---|---|---|---|
| 1 | S-FANA gap (10 DNA) | S-<u>ATA T</u>cc ttg tcg ta<u>T CCC</u> | 64 |
| 2 | S-FANA gap (8 DNA) | S-<u>ATA TC</u>c ttg tcg t<u>AT CCC</u> | 65 |
| 3 | S-FANA gap (6 DNA) | S-<u>ATA TCC</u> ttg tcg <u>TAT CCC</u> | 68 |
| 4 | S-FANA gap (4 DNA) | S-<u>ATA TCC T</u>tg tc<u>G TAT CCC</u> | 70 |
| 5 | S-FANA gap (2 × 1 DNA) | S-<u>ATA TCC TTg TCg TAT CCC</u> | 71 |
| 6 | S-FANA | S-<u>ATA TCC TTG TCG TAT CCC</u> | 72 |
| 7 | PO-FANA | O-<u>ATA TCC TTG TCG TAT CCC</u> | 82 |

TABLE 1-continued

Antisense oligonucleotide (AON) sequences and melting temperatures (Tm) of duplexes of AON with complementary target RNA[a]

| ID # | AON Designation | AON Sequence[b] | Tm (° C.)[c] |
|---|---|---|---|
| 8 | 2'OMe gap (10 DNA) | S-<u>ATA T</u>cc ttg tcg ta<u>T CCC</u> | 66 |
| 9 | 2'OMe gap (6 DNA) | S-<u>ATA TCC</u> ttg tcg <u>TAT CCC</u> | 68 |
| 10 | 2'OMe gap (4 DNA) | S-<u>ATA TCC T</u>tg tc<u>G TAT CCC</u> | 72 |
| 11 | S-DNA | S-ata tcc ttg tcg tat ccc | 62 |
| 12 | PO-DNA | O-ata tcc ttg tcg tat ccc | 70 |

[a]Aqueous solutions of 2.5 × 10$^{-6}$ M of duplex. Buffer: 140 nM KCl, 1 mM MgCl$_2$, 5 mM Na$_2$HPO$_4$ (ph 7.2).
[b]code: <u>N</u> = FANA nucleotide; n = DNA nucleotide; <u>N</u> = 2'OMe-RNA nucleotide; S- = containing phosphorothioate bonds; PO- = containing phosphodiester bonds.
[c]±1° C.

EXAMPLE 2

Efficacy of Various Antisense Oligonucleotides to Inhibit Intracellular Gene Expression Antisense oligonucleotides have the potential to inhibit expression of virtually any gene, based on the specific base sequence of the chosen target mRNA. We studied the ability of antisense oligonucleotides constructed from 2'-deoxy-2'-fluoro-β-D-arabinonucleotides (FANA) flanking a series of 2'-deoxyribose nucleotide residues of variable length (S-FANA gapmer) to interfere with the expression of a well-characterized marker model, namely expression of the enzyme luciferase, in cells stably transfected with the luciferase gene. The efficacy of the S-FANA gapmer to inhibit intracellular luciferase expression was compared with identical sequence antisense oligonucleotides constructed entirely from 2'-deoxy-2'-fluoro-β-D-arabinonucleotides or entirely from 2'-deoxyribonucleotides. Linkages between nucleotides were either phosphodiester (PO) or phosphorothioate (PS). The specific antisense oligonucleotide sequences were 5'-ATA TCC TTG TCG TAT CCC-3', which is complementary to bases 1511-1528 of the coding region of the luciferase gene. As a control, randomized oligonucleotide sequences (5'-TAA TCC CTA TCG TCG CTT-3') were used; these are of the same base composition as the specific AON sequence, but have no complementarity to any portion of the luciferase gene. These randomized oligonucleotides were unable to effect inhibition of target luciferase expression.

The ability of oligonucleotides complementary to a specific region of mRNA coding for luciferase was tested for inhibition of luciferase activity expression in Hela X1/5 cells (obtained from the European Collection of Cell Cultures, Salisbury, UK). Hela X1/5 cells are stably transfected with the luciferase gene and express functional luciferase enzyme.

Oligonucleotides were delivered to the cells by complexing the oligonucleotide with cytofectin GSV GS3815 (Glen Research, Sterling, Va., USA). Briefly, oligonucleotides were diluted with DMEM in the absence of fetal bovine serum (FBS) to provide a final concentration of oligonucleotide 10-fold higher than the final concentration to which the cells would be exposed. Cytofectin GSV was prepared in serum-free DMEM at a final concentration of 25 μg/ml. Equal volumes of oligonucleotide and cytofectin solutions were mixed in polystyrene plastic and incubated for 15 min at room temperature, then the mixture was diluted 5-fold with DMEM. containing 10% FBS.

X1/5 cells were plated in 96-well plates at a density of 1.5-2×10$^4$ cells/well and allowed to grow for 24 h in DMEM/ 10% FBS. This generally provided a cell density of 80% confluence, as assessed by microscopy. The culture medium was then removed from the cells, the cells were washed several times with phosphate-buffered saline, and then overlayed with the medium containing the oligonucleotide/cytofectin mixture. After 24 h incubation, the Hela cells were harvested, homogenized and assayed for luciferase activity. Luciferase activity was assayed by a luminometric method using the luciferase assay kit components obtained from Promega (Madison, Wis., USA).

The results of an experiment comparing the ability of antisense oligonucleotides (sequence 5'-ATA TCC TTG TCG TAT CCC-3'), constructed from a variety of different nucleotide and linkage chemistries, to inhibit X1/5 cell luciferase activity is given in FIG. 1. In all cases, the cells were exposed to a final concentration of 250 nM of antisense oligonucleotide, for 24 h prior to assay of luciferase activity. The antisense oligonucleotide constructed entirely from β-D-2'-deoxyribose with phosphodiester bonds (PO-DNA, ID# 12 in Table 1) was unable to effect any inhibition of X1/5 cell luciferase activity, whereas the antisense oligonucleotide constructed entirely from β-D-2'-deoxyribose with phosphorothioate bonds (PS-DNA; ID# 11 in Table 1) provided approximately 60% inhibition. Antisense oligonucleotides constructed entirely from 2'-deoxy-2'-fluoro-β-D-arabinonucleotides with either phosphodiester bonds (PO-FANA; ID# 7 in Table 1) or phosphorothioate bonds (PS-FANA; ID# 6 in Table 1) provided approximately 55% and 25% inhibition of luciferase activity, respectively. Under the same conditions, the antisense oligonucleotide constructed from 2'-deoxy-2'-fluoro-β-D-arabinonucleotides flanking a series of ten 2'-deoxyribose nucleotide residues, all joined with phosphorothioate bonds (S-FANA gapmer; ID# 1 in Table 1), provided at least a 90% inhibition of X1/5 cell luciferase activity. No obvious cell toxicity was noted with any of the antisense oligonucleotides under the conditions used in this experiment.

The results (FIG. 1) show that the S-FANA gapmer (10 DNA gap) is a significantly better inhibitor of X1/5 cell luciferase activity expression than any of PO-DNA, S-DNA, PO-FANA or S-FANA. X1/5 cells were incubated with various antisense oligonucleotides (250 nM final concentration), all directed against the same target sequence of luciferase mRNA. Following appropriate incubation, the residual level of intracellular luciferase activity was determined.

EXAMPLE 3

Comparison of S-DNA and S-FANA Gapmer (10 DNA) Antisense Oligonucleotides to Inhibit Intracellular Gene Expression Solutions of S-DNA (ID# 11, Table 1) and S-FANA gapmer (ID# 1, Table 1) were prepared with Cytofectin GSV GS3815 as described in Example 2. Hela X1/5 cells were plated in replicate 6-well plates at a density of 5×10$^5$ cells/ well and allowed to grow for 24 h in DMEM/10% FBS. The culture medium was then removed from the cells, the cells were washed several times with phosphate-buffered saline, and then overlayed with the medium containing the oligonucleotide/cytofectin mixture. After 24 h incubation, the Hela X1/5 cells were harvested and treated in a manner appropriate for the subsequent assay procedures (described below).

(a) Assay for Luciferase Enzyme Activity

Luciferase enzyme activity assays were performed using the luciferase assay kit system from Promega, Madison, Wis., USA, according to the manufacturer's protocol. Briefly, cells were washed with phosphate-buffered saline and then lysed with the cell lysis buffer provided in the kit. Replicate aliquots of the cell lysates were transferred to 96 well assay plates. Luciferin substrate solution was added and luminescence was measured immediately using a SPECTRAmax GEMINI XS microplate spectrofluorometer (Molecular Devices, Sunnyvale, Calif., USA) set at the luminescence reading mode. Results were normalized for any variation in total cell protein concentration in the individual samples (determined using the Bio-Rad protein assay reagent on identical aliquots).

(b) Assay for Luciferase Protein Expression.

Levels of luciferase protein in antisense-treated and untreated X1/5 cells were determined by Western blot analysis. Protein extracts of X1/5 cells were prepared by lysing the cells in the same lysis buffer used for preparation of the samples for luciferase enzyme assays, followed by clarification by centrifugation. The protein content of individual samples was measured using the Bio-Rad protein assay reagent (Bio-Rad, Hercules, Calif., USA). Samples containing identical amounts of cell protein (approximately 20 μg) were subjected to SDS-PAGE, then transferred to nitrocellulose membranes (0.45μ). The membrane was incubated in TTBS (20 mM Tris-HCl containing 500 mM NaCl and 0.05% Tween 20) containing 5% skim milk for at least one hour. The blots were then incubated with a goat antibody specifically reacting with firefly luciferase (obtained from Chemicon International Inc, Temecula, Calif., USA), using antibody at a concentration of 1 mg/ml in TTBS. After 1 h incubation, the membranes were washed extensively with TTBS, then incubated with horseradish peroxidase-conjugated anti-goat IgG (Chemicon International Inc., Temecula, Calif., USA) at a 1:10,000 dilution in TTBS. The peroxidase-reactive regions were then detected using the Renaissance Western blot Chemiluminescene Reagent Kit (NEN Life Science Products, Boston, Mass., USA) and Kodak X-OMAT film, according to manufacturer's instructions. Luciferase protein levels were then quantified by densitometric analysis of the developed film.

(c) Assay for Luciferase mRNA.

The isolation of total RNA from X1/5 cells and Northern blot assays for luciferase mRNA levels were carried. Normalized amounts of total cell RNA (10-20 μg) were size-fractionated on 1% agarose gels containing 2.2 M formaldehyde then transferred to 0.45μ nitrocellulose membranes (Bio-Rad, Hercules, Calif., USA). The hybridization probe for luciferase mRNA was $^{32}$P-internally labeled DNA derived from the full-length cDNA for the firefly luciferase gene (from plasmid pGEM-Luc, Promega, Madison, Wis., USA) generated using the oligolabeling kit from Amersham-Pharmacia Biotech (Piscataway, N.J., USA). Hybridization of the radiolabeled probe with membrane bound RNA was carried out in 6×SSC buffer (900 mM sodium chloride containing 90 mM sodium citrate at pH 7.0) containing 50% formamide, 0.5% sodium dodecyl sulfate and blocking reagents. Hybridizations were carried out at 42° C. for 16 hours. The membranes were then washed twice with 1×SSC containing 0.1% SDS at room temperature, then 0.1×SSC containing 0.1% SDS at room temperature, and finally 1×SSC containing 0.5% SDS at 42° C. Membrane-associated radioactivity was localized by autoradiography, and quantified by densitometry.

Figures 2A, 2B, 2C:
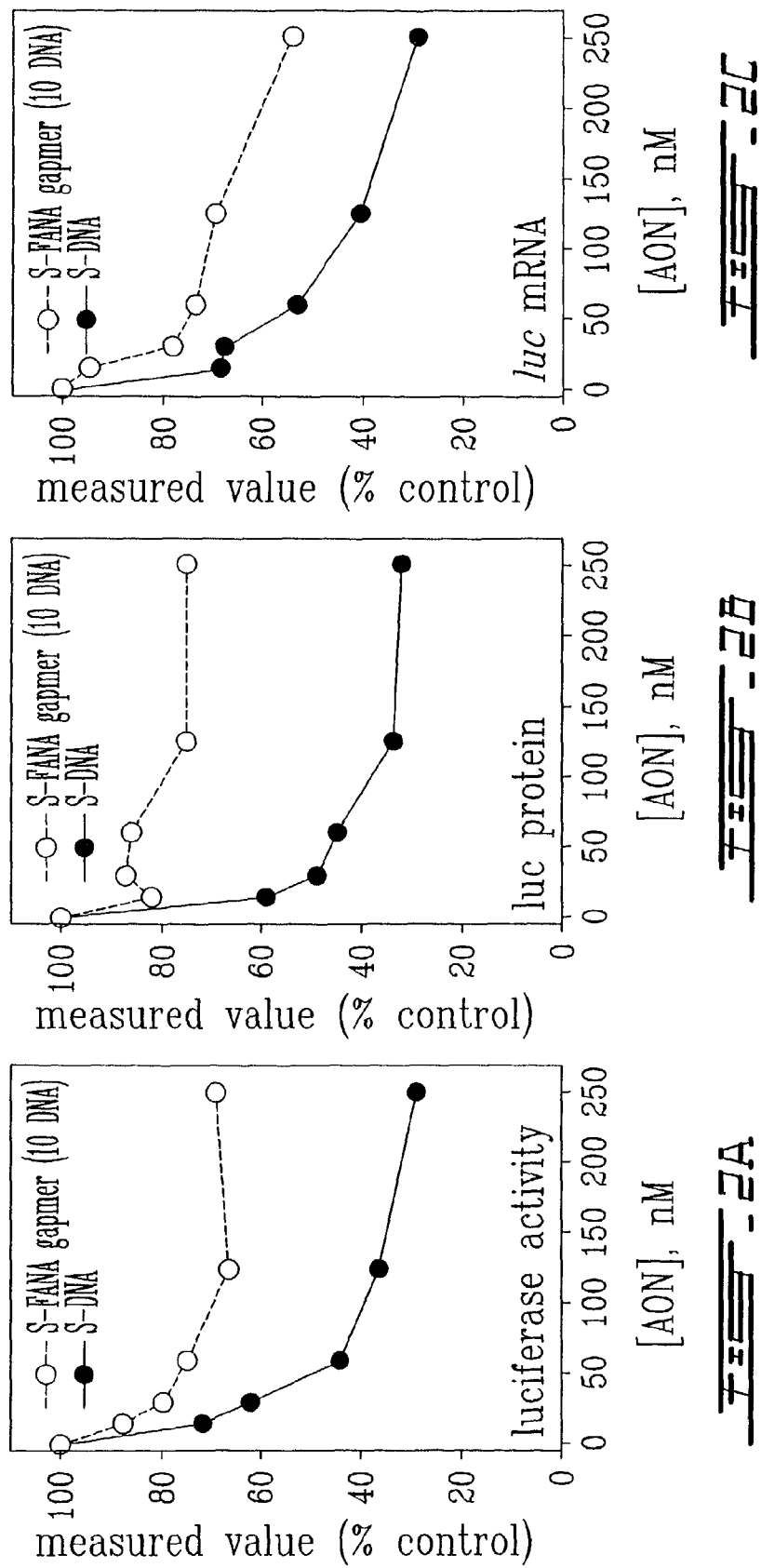
FIGS. 2A-C illustrate the comparison of PS-DNA and PS-FANA gapmer (10 DNA) antisense oligonucleotides to inhibit intracellular gene expression.

The results of FIG. 2 show that S-FANA gapmer (10 DNA) was significantly more effective than S-DNA at inhibiting X1/5 cell luciferase activity over a range of concentrations varying from 15 nM to 250 nM antisense oligonucleotide (panel A).

Treatment of X1/5 cells with the S-FANA gapmer (10 DNA) resulted in a dose-dependent decrease in total luciferase protein (panel B) that was not evident in cells treated with the S-DNA antisense. In addition, treatment of X1/5 cells with the S-FANA gapmer (10 DNA) resulted in a dose-dependent decrease in total luciferase mRNA (panel C); this decrease was greater than that effected by the S-DNA antisense. Luciferase protein levels were assessed by Western blot analysis using an antibody specifically directed towards luciferase. Luciferase mRNA levels were assessed by Northern blot analysis using a DNA probe specifically directed towards a sequence of the luciferase mRNA.

EXAMPLE 4

Effect of Treatment with S-DNA and S-FANA Gapmer (10 DNA) Antisense Oligonucleotides on Cellular Luciferase Protein and mRNA Solutions of S-DNA (ID# 11, Table 1) and S-FANA gapmer (D# 1, Table 1) were prepared with Cytofectin GSV GS3815 as described in Example 2. Hela X1/5 cells were plated in replicate 6-well plates at a density of 5×10⁵ cells/well and allowed to grow for 24 h in DMEM/10% FBS. The culture medium was then removed from the cells, the cells were washed several times with phosphate-buffered saline, and then overlayed with the medium containing the oligonucleotide/cytofectin mixture to provide the indicated final concentrations of S-DNA or S-FANA gapmer (10 DNA) antisense oligonucleotides. After 24 h incubation, the Hela X1/5 cells were harvested and treated in a manner appropriate for analysis of luciferase protein levels or luciferase mRNA levels, exactly as described in Example 3.

Figure 3A:
FIGS. 3A-B illustrate the effect of treatment with PS-DNA and PS-FANA gapmer (10 DNA) antisense oligonucleotides on cellular luciferase protein and mRNA.
Figure 3A:
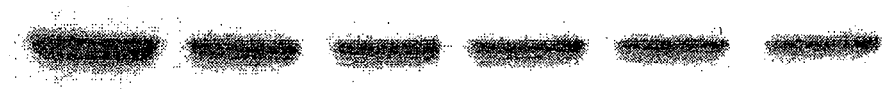
Figure 3B:
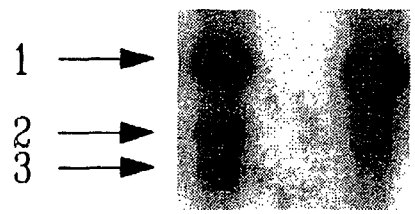

The results in FIG. 3, panel (A), show the Western blot analysis of luciferase protein levels in extracts of X1/5 cells treated with varying concentrations of S-DNA (upper series) or S-FANA gapmer (10 DNA) (lower series). (A) Variation in luciferase protein levels following exposure of X1/5 cells to increasing amounts of either PS-DNA or PS-FANA gapmer (10 DNA) antisense oligonucleotides.

It is readily seen that the cells treated with S-FANA gapmer (10 DNA) show a dose-dependent decrease in total luciferase protein, whereas this effect is much less apparent in cells treated with S-DNA. Quantitation of the luciferase protein levels is provided in panel (B) of FIG. 2. (B) The PS-FANA gapmer (10 DNA) antisense oligonucleotide elicits RNaseH cleavage of intracellular luciferase mRNA. 1 corresponds to the full-length luciferase mRNA, 2 and 3 are the cleaved products. + represents mRNA isolated from cells treated with 250 nM PS-FANA gapmer (10 DNA), − represents mRNA isolated from cells not exposed to antisense.

The results in FIG. 3, panel (B), show that treatment of X1/5 cells with 250 nM S-FANA gapmer (10 DNA) results in a readily discernible cleavage of luciferase rnRNA (lane +). Three species of luciferase mRNA are seen, full-length (1), and two smaller species (2 and 3) that correspond to the cleavage products expected from RNaseH degradation of the full-length mRNA in the region targeted by the antisense oligonucleotide. The luciferase mRNA profile in cells not exposed to any antisense is shown in the lane marked (−).

EXAMPLE 5

Effect of DNA "Gap" Size on the Ability of Gapmer Antisense Oligonucleotides to Inhibit Cellular Specific Gene Expression We compared antisense oligonucleotides constructed from 2'-deoxy-2'-fluoro-β-D-arabinonucleotides (FANA) flanking a series of 2'-deoxyribose nucleotide residues of variable length with phosphorothioate internucleotide linkages (S-FANA gapmer) to similar MBO constructed with 2'-O-methyl RNA wings, and to non-gapmer PS-DNA and PS-FANA oligonucleotides, in their ability to inhibit the expression of intracellular luciferase activity in Hela X1/5 cells. The specific antisense oligonucleotide sequence was 5'-ATA TCC TTG TCG TAT CCC-3', which is complementary to bases 1511-1528 of the coding region of the luciferase gene.

Oligonucleotides were delivered to the cells by complexing the oligonucleotide with cytofectin GSV GS3815 (Glen Research, Sterling, Va., USA), exactly as described for Example 2.

X1/5 cells were plated in 96-well plates at a density of 1.5-2×10⁴ cells/well and allowed to grow for 24 h in DMEM/10% FBS. The culture medium was then removed from the cells, the cells were washed several times with phosphate-buffered saline, and then overlayed with the medium containing the oligonucleotide/cytofectin mixture, to provide a final concentration of 250 nM of antisense oligonucleotide. After 24 h incubation, the Hela cells were harvested, homogenized and assayed for luciferase activity by a luminometric method using the luciferase assay kit components obtained from Promega (Madison, Wis., USA).

Figure 4:
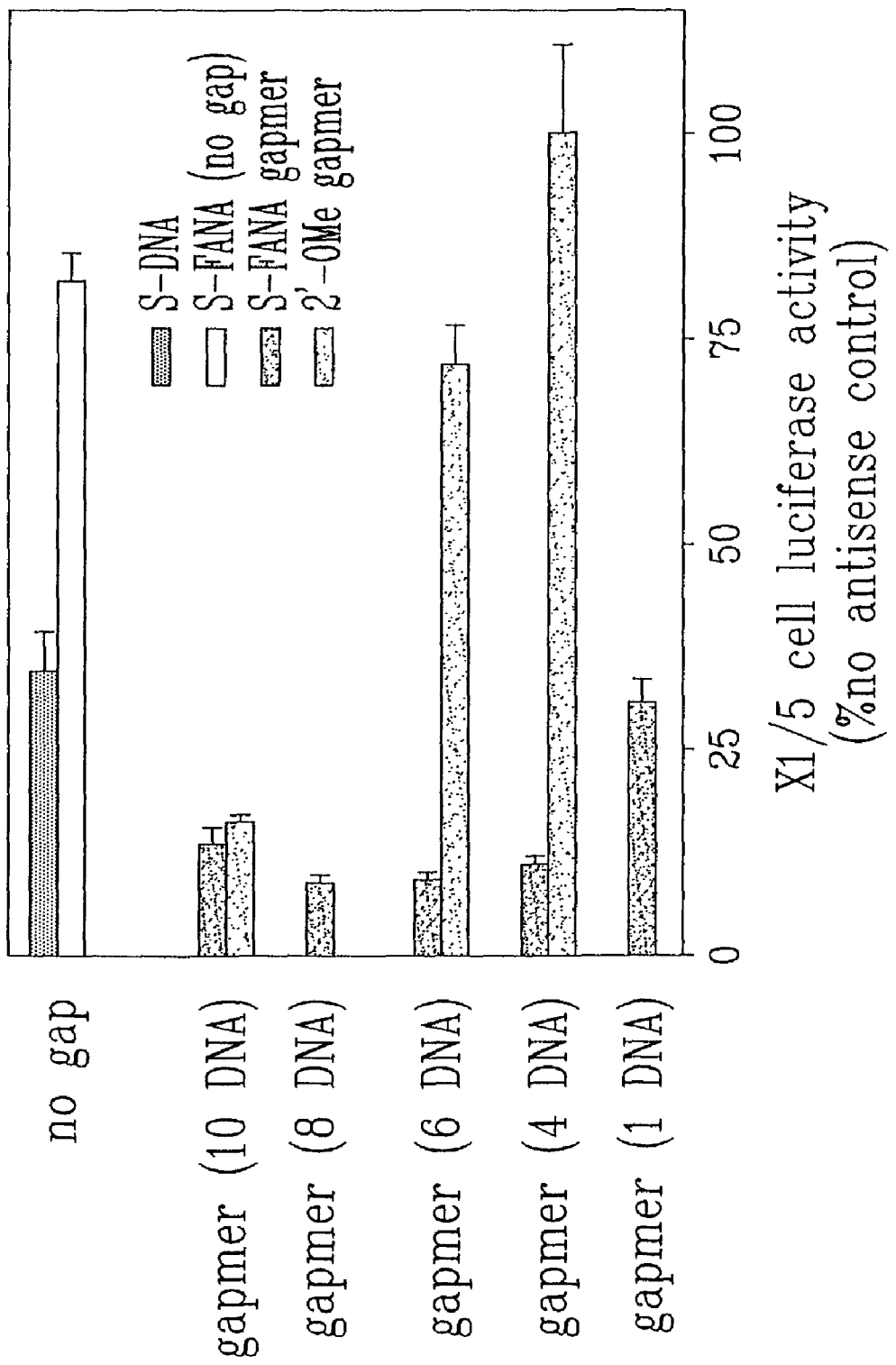
FIG. 4 illustrates the effect of DNA "gap" size on the ability of gapmer antisense oligonucleotides to inhibit cellular specific gene expression.

The results of an experiment comparing the ability of antisense oligonucleotides (sequence 5'-ATA TCC TTG TCG TAT CCC-3'), constructed from a variety of different nucleotide, to inhibit X1/5 cell luciferase activity is given in FIG. 4. The data represent residual intracellular luciferase activity following exposure to a final concentration of 250 nM antisense oligonucleotide. All antisense were directed to the same sequence of luciferase mRNA. S-DNA is PS-DNA, S-FANA is PS-FANA without a DNA gap, S-FANA gapmer is an antisense oligonucleotide constructed from 2'-fluoroarabinonucleotides flanking a series of deoxyribose nucleotide residues of defined length (indicated), 2'-OMe gapmer is an antisense oligonucleotide constructed from 2'-O-methylribonucleotides flanking a series of deoxyribose nucleotide residues of defined length (indicated).

In all cases, the cells were exposed to a final concentration of 250 nM of antisense oligonucleotide, for 24 h prior to assay of luciferase activity. The antisense oligonucleotide constructed entirely from β-D-2'-deoxyribonucleotides with phosphorothioate bonds (S-DNA; ID# 11 in Table 1) inhibited luciferase expression by about 65%, whereas that constructed entirely from β-D-2'-deoxy-2'F-arabinonucleotides with phosphorothioate bonds (S-FANA; ID# 6 in Table 1) was much less effective, providing only an average of 20% inhibition of luciferase expression. Both S-FANA and 2'-O-methyl RNA MBO gapmers with a ten DNA gap segment (ID# 1 and 8, respectively, in Table 1) were equally and very effective inhibitors, providing an approximate 85-90% decrease in intracellular luciferase activity. However, the antisense activity of 2'-O-methyl RNA MBO gapmers decreased dramatically with decreasing size of the DNA gap; indeed, the 2'-O-methyl RNA MBO gapmer with a 4 DNA gap (ID# 10, Table 1) showed little or no inhibitory activity against X1/5 cell luciferase expression. In sharp contrast, the antisense activity of the S-FANA was unaffected with decreasing DNA gaps, down to a 4 DNA length. Interestingly, the antisense activity of the S-FANA gapmer with a single DNA gap (ID# 5, Table 1) was as good as that of the corresponding all S-DNA oligonucleotide (D# 11, Table 1). This was unexpected, since the all S-FANA oligonucleotide was very poor in this respect.

The results of this experiment show that MBO antisense oligonucleotides constructed with wings comprised of S-FANA show minimal dependence on DNA gap size, unlike the strong DNA gap size dependence exhibited by the corresponding MBO constructed with wings comprised of S-2'-O-methyl RNA.

EXAMPLE 6

Effect of DNA "Gap" Size on the Ability of Gapmer Antisense Oligonucleotides to Inhibit Cellular Specific Gene Expression—Effect of Antisense Oligonucleotide Concentration In order to better define the antisense activity of S-FANA gapmers compared to S-2'-O-methyl RNA gapmer MBO, we studied the dose-response relationships of inhibition of X1/5 cell luciferase expression as a function of antisense oligonucleotide concentration.

X1/5 cells were plated in 96-well plates at a density of $1.5-2 \times 10^4$ cells/well and allowed to grow for 24 h in DMEM/10% FBS. The culture medium was then removed from the cells, the cells were washed several times with phosphate-buffered saline, and then overlayed with the medium containing the oligonucleotide/cytofectin mixture, to provide final concentrations of antisense oligonucleotides ranging from 0 to 250 nM. After 24 h incubation, the Hela cells were harvested, homogenized and assayed for luciferase activity by a luminometric method using the luciferase assay kit components obtained from Promega (Madison, Wis., USA).

The results of this experiment are shown in FIG. 5 (panels A and B). The data represent residual intracellular luciferase activity following exposure of X1/5 cells to the various indicated final concentrations of antisense oligonucleotide. All antisense were directed to the same sequence of luciferase mRNA. S-DNA is PS-DNA, S-FANA gapmer is an antisense oligonucleotide constructed from 2'-fluoroarabinonucleotides flanking a series of deoxyribose nucleotide residues of defined length (indicated), OMe gapmer is an antisense oligonucleotide constructed from 2'-O-methylribonucleotides flanking a series of deoxyribose nucleotide residues of defined length (indicated).

In FIG. 5A, it can be seen that all of the S-FANA gapmers with gaps between 4 and 10 S-DNA nucleotides were very effective inhibitors of intracellular luciferase expression, much better than S-DNA alone. The $IC_{50}$ values for this inhibition ranged from about 15 nM (for the 10 DNA gap; ID# 1, Table 1) to <<15 nM (for the 8, 6 and 4 DNA gap oligonucleotides; ID# 2, 3 and 4 respectively, in Table 1). In contrast, the $IC_{50}$ value for S-DNA (ID# 11, Table 1) antisense inhibition was about 100 nM. The $IC_{50}$ for the S-FANA MBO with 1 DNA gaps (ID# 5, Table 1) was identical to that of the all S-DNA oligonucleotide.

In FIG. 5B, it can be seen that the $IC_{50}$ for the ability of the S-2'-O-methyl RNA gapmer (10 DNA gap; ID# 8, Table 1) was essentially identical to that of the corresponding S-FANA gapmer (ID# 1, Table 1). In contrast, the $IC_{50}$ values for the antisense activity of the other S-2'-O-methyl RNA gapmers tested (6 and 4 DNA gaps; ID# 9 and 10 respectively in Table 1) were >>250 nM. Indeed, the latter gapmers were virtually ineffective as antisense inhibitors of X1/5 cell luciferase expression.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. An oligonucleotide 'chimera' to selectively prevent gene expression in a sequence-specific manner, consisting of a chimera of modified arabinose and 2'-deoxy sugars consisting of the formula:

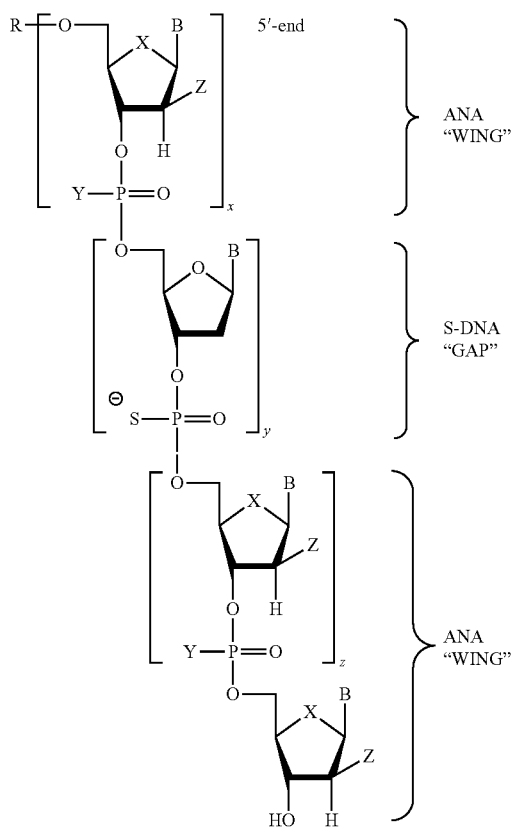

wherein,
  $x \geq 1$, $y \geq 1$, and $z \geq 0$;
  R is selected from a group consisting of hydrogen, thiophosphate, and a linker moiety that enhances cellular uptake of such oligonucleotide;
  B is selected from the group consisting of adenine, guanine, uracil, thymine, cytosine, inosine, and 5-methylcytosine;
  Y at the internucleotide phosphate linkage is sulfur;
  X at the furanose ring (position 4') is selected from the groups oxygen, sulfur, and methylene ($CH_2$);
  Z at the 2' position of the sugar ring is selected from the group consisting of a halogen, alkyl, alkylhalide, allyl, amino, aryl, alkoxy, and azido; and, wherein the modified arabinose sugars are in D-configuration.

2. A method for cleaving single stranded RNA in vitro, which comprises the steps of:
  (a) hybridizing in a sequence specific manner the oligonucleotide of claim 1 to a single stranded RNA to induce RNase H activity; and
  (b) allowing said induced RNase H to cleave said hybridized single stranded RNA.

3. A method to prevent translation in vitro of single stranded RNA, which comprises hybridizing in a sequence specific manner the oligonucleotide of claim 1 to single stranded RNA, and thereby prevent production of a specific protein encoded by said single stranded RNA.

4. The method of claim 2, wherein said RNA is complementary RNA.

5. The method of claim 4, wherein said complementary RNA is cellular mRNA or viral RNA.

6. The oligonucleotide of claim 1, comprising modified arabinonucleotide residues, flanking a series of deoxyribose nucleotide residues of variable length, wherein the series of deoxyribose nucleotide residues comprises a gap of $\leq 10$ deoxyribose nucleotide residues.

7. The oligonucleotide of claim 1, comprising modified arabinonucleotide residues, flanking a series of deoxyribose nucleotide residues of variable length, wherein the series of deoxyribose nucleotide residues comprises a gap of 10 deoxyribose nucleotide residues.

8. The oligonucleotide of claim 1, comprising modified arabinonucleotide residues, flanking a series of deoxyribose nucleotide residues of variable length, wherein the series of deoxyribose nucleotide residues comprises a gap of 8 deoxyribose nucleotide residues.

9. The oligonucleotide of claim 1, comprising modified arabinonucleotide residues, flanking a series of deoxyribose nucleotide residues of variable length, wherein the series of deoxyribose nucleotide residues comprises a gap of 6 deoxyribose nucleotide residues.

10. The oligonucleotide of claim 1, comprising modified arabinonucleotide residues, flanking a series of deoxyribose nucleotide residues of variable length, wherein the series of deoxyribose nucleotide residues comprises a gap of 4 deoxyribose nucleotide residues.

11. The oligonucleotide of claim 1, comprising modified arabinonucleotide residues, flanking a series of deoxyribose nucleotide residues of variable length, wherein the series of deoxyribose nucleotide residues comprises a gap of 2×1 deoxyribose nucleotide residues.

12. The method of claim 3, wherein said RNA is complementary RNA.

13. The method of claim 12, wherein said complementary RNA is cellular mRNA or viral RNA.

14. The oligonucleotide of claim 1, wherein the oligonucleotide hybridizes to a single stranded RNA to induce nuclease stability.

15. The oligonucleotide of claim 1, wherein Z is fluorine.

16. The oligonucleotide of claim 1, wherein X is oxygen.

17. The oligonucleotide of claim 1, wherein the oligonucleotide hybridizes to a single stranded RNA with increased binding strength of hybridization compared to a native DNA oligonucleotide having the same sequence.

18. The oligonucleotide of claim 1, wherein the oligonucleotide hybridizes to a single stranded RNA to induce increased permeability of said oligonucleotide into cells.

19. The oligonucleotide of claim 1, wherein the oligonucleotide hybridizes to a single stranded RNA to induce cleavage of target RNA by RNaseH.

20. The oligonucleotide of claim 1, wherein the oligonucleotide hybridizes to a single stranded RNA to induce physical blockage of ribosome translocation ('translation arrest').

21. The oligonucleotide of claim 1, wherein Z is fluorine, X is oxygen and Y is sulphur.

* * * * *